United States Patent [19]

Ku et al.

[11] Patent Number: 5,562,831
[45] Date of Patent: Oct. 8, 1996

[54] METHOD FOR SEPARATION OF GIBBERELLIN MIXTURES

[75] Inventors: Yi-Yin Ku, Buffalo Grove; David P. Sawick, Wildwood, both of Ill.

[73] Assignee: Abbott Laboratories, Abbott Park, Ill.

[21] Appl. No.: 146,108

[22] PCT Filed: Jun. 12, 1992

[86] PCT No.: PCT/US92/05016

§ 371 Date: Nov. 10, 1993

§ 102(e) Date: Nov. 10, 1993

[87] PCT Pub. No.: WO92/22544

PCT Pub. Date: Dec. 23, 1992

Related U.S. Application Data

[63] Continuation-in-part of Ser. No. 715,531, Jun. 14, 1991, abandoned.

[51] Int. Cl.$^6$ .................................................. C07D 307/94
[52] U.S. Cl. ............................................ 210/638; 210/192
[58] Field of Search ..................................... 210/638, 634, 210/727, 728, 192; 71/91, 92; 549/297

[56] References Cited

U.S. PATENT DOCUMENTS

| | | |
|---|---|---|
| 4,243,594 | 1/1981 | Beale et al. . |
| 4,282,154 | 8/1981 | Lischewski et al. . |
| 4,532,334 | 7/1985 | Turner et al. . |
| 4,931,082 | 6/1990 | Elliott et al. . |

FOREIGN PATENT DOCUMENTS 1174924  12/1969  United Kingdom .

OTHER PUBLICATIONS

Park, K. H., Han'guk Nonghwa Hakhoechi 28(2):82–87 (1985).

*Primary Examiner*—Frank Spear
*Attorney, Agent, or Firm*—Andreas M. Danckers; Michael J. Ward

[57] ABSTRACT

A method for the separation of gibberellins from mixtures thereof by selective silylation or desilylation, as well as substantially pure gibberellins prepared thereby.

10 Claims, No Drawings

METHOD FOR SEPARATION OF GIBBERELLIN MIXTURES

This application is a continuation-in-part of U.S. patent application Ser. No. 07/715,531, filed on Jun. 14, 1991, now abandoned.

TECHNICAL FIELD

The present invention relates to novel methods for the separation of the commercially available mixture of gibberellins, and especially gibberellins GA4 and GA7, and to the products made by such separation processes.

BACKGROUND OF THE INVENTION

Gibberellins are powerful plant hormones which are responsible for flowering, root growth, stem elongation, fruit size, branching and the like for various fruits and crops. The mixture of gibberellins GA4 and GA7 and pure GA3 are the only gibberellins presently commercially produced in quantity from cultures of the fungus Gibberella fujikoroi. These gibberellins are, therefore, convenient starting materials for the synthesis of less accessible gibberellins and, themselves, are powerful plant hormones which are important for use in agriculture.

There has been a long-standing need for a method which effectively separates GA4 and GA7 from the above mixture. Previously, tedious reverse-phase high performance liquid chromatography (HPLC) was used for separation of the mixture of GA4 and GA7. This process was labor intensive and not feasible for the preparation of large quantities. Some laboratory scale chemical processes have been used for the preparation of GA4 and GA7 in small quantities. However, these processes all involve multiple step syntheses. For example, as described in U.S. Pat. No. 4,243,594, GA7 is obtained from GA3 by a five step reaction sequence which involves selective protection of the 3-β-hydroxyl group of GA3, preparation of the 13-methanesulfonyl derivative of the 3-acetate, hydrolysis of the acid chloride and reduction of the bridgehead-methanesulfonate, followed by hydrolysis of the resulting acetate. As described in U.S. Pat. No. 4,532,334, GA4 is obtained via Jones oxidation of a GA4/GA7 mixture, followed by Selectride® reduction. Another method for obtaining GA4 is selective degradation of GA7 from the mixture of GA4 and GA7, followed by isolation of GA4; but this method literally converts the GA7 into degradation products. None of these methods can provide GA4 and GA7 in large quantities efficiently. Alternatively, some authors have proposed the derivatization of gibberellins, including the formation of methyl esters and trimethylsilyl ethers, as a means of improving their detection and monitoring during analytical separation. Park, for example, in the Korean publication Han'guk Nonghwa Hakhoechi, 28(2):82–87 (1985), discloses the formation of such derivatives in connection with analysis by gas chromatography-mass spectroscopy. However, no suggestion is made that certain gibberellins may be selectively derivatized as is accomplished in the present invention, or that gibberellins so derivatized are more readily separated. Moreover, the above methods are for analytical rather than production use. Consequently, the need remains for an effective, large-scale separatory procedure.

SUMMARY OF THE INVENTION

It has now been found that pure GA4 and pure GA7 can be obtained efficiently by using a process of either (i) selective silylation and separation, or (ii) silylation, selective desilylation and separation. This process has also been found to be useful in the separation of mixtures of other gibberellins, such as GA 1 and GA3, where one gibberellin undergoes silylation/desilylation more readily than another.

Accordingly, in one aspect of the present invention is disclosed a process for separating gibberellins from mixtures thereof, and especially GA4 and GA7 from a mixture of GA4 and GA7, which comprises reacting said mixtures with a silylating agent. This reaction may be followed, in the case of GA4 and GA7, by selectively hydrolyzing the GA7 silyl ether in the presence of the GA4 silyl ether and separating the GA7 from the GA4 silyl ether. Preferably, the silylating agent in the above process is t-butyldimethylsilyl chloride.

In another aspect of the invention is disclosed a gibberellin selected from the group consisting of GA4 and GA7 which is prepared by the above process.

In yet another aspect of the invention are disclosed substantially pare compounds of the formulae:

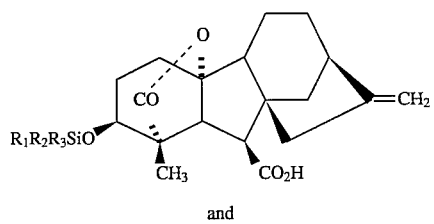

and

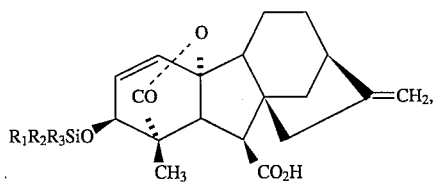

wherein $R_1$, $R_2$ and $R_3$ are independently selected from loweralkyl and aryl. Preferred among such compounds are those wherein $R_1$ is t-butyl and $R_2$ and $R_3$ are methyl.

The term "loweralkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "aryl" as used herein refers to phenyl, benzyl, diphenylmethyl or triphenylmethyl or substituted phenyl, benzyl, diphenylmethyl or triphenylmethyl wherein one or more of the phenyl rings is substituted with loweralkyl, halogen or alkoxy.

The term "alkoxy" as used herein refers to R'O— wherein R' is a loweralkyl group.

DETAILED DESCRIPTION OF THE INVENTION

The present invention relates to novel processes for obtaining pure GA4 and GA7 from the readily available mixture of GA4 and GA7. The methods of this invention are; predicated upon the discovery of the differential reactivities of GA4 and GA7 toward silyl ether formation and subsequent deprotection.

It has been discovered that GA4 and GA7 each react differently with triloweralkylsilyl chloride in the presence of imidazole in dimethylformamide (DMF). For example, GA7 reacts with t-butyldimethylsilyl chloride in the presence of imidazole in DMF at room temperature to form the silyl ether, while GA4 is inactive under these conditions (see Scheme I below).

This selectivity for silylation of GA7 versus GA4 may be attributed to the more accessible steric enviroment of the ting A of GA7 (more planar) than the ting A of GA4. Selective reaction was achieved by using slightly more than one equivalent (1.6 eq.) of t-butyldimethylsilyl chloride at room temperature. Increasing the amount of silylating agent in excess of this amount or raising the temperature above room temperature resulted in the formation of the silyl ether of GA4. Under forcing conditiona, such as higher temperature (45° C.) and/or excess silylating agent (5 eq.), both GA4 and GA7 can be completely converted to their silyl ethers. Other silylating agents can include alkyl or aryl substituted silylating agents (e.g., $R_1R_2R_3SiX$ wherein $R_1$, $R_2$ and $R_3$ are independently selected from loweralkyl and aryl and X romethane; however, the silyl ether of GA7 is much less soluble than GA4 in acetic acid and water. Based on these differences, the silyl ether of GA7 can be easily separated from GA4 by simple crystallization. The separated silyl ether of GA7 can then be desilylated by simply treating it with a desilylating agents such as tetrabutylammonium fluoride to afford GA7. Other useful desilylating agents include $K_2CO_3$/methanol, H+/methanol (wherein the acidic reagent is an acidic resin such as Dowex® 50W-X8 or Nafion® and the like), KF/crown ether, HF, $BF_3.Et_2O$, $FeCl_3$/acetic anhydride, acetic acid/water or citric acid/methanol and the like.

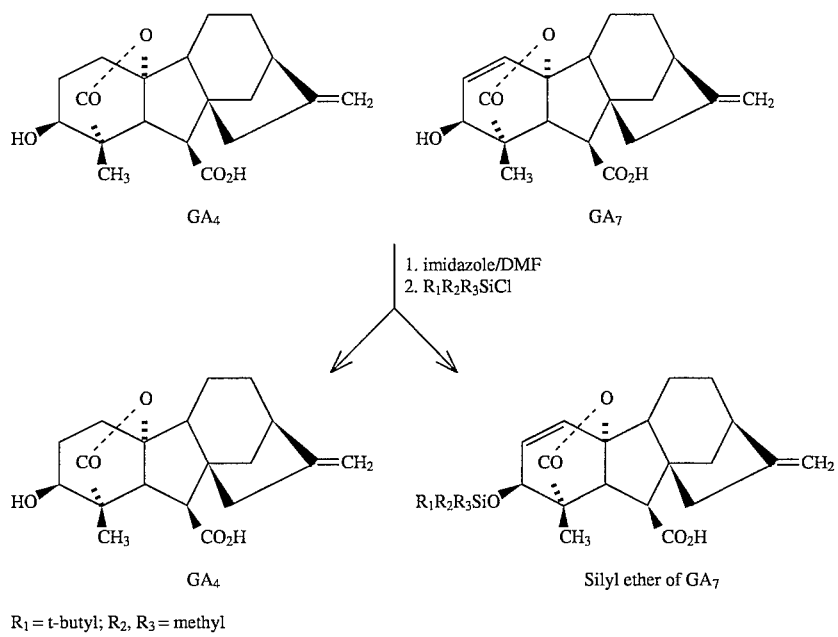

SCHEME 1

$R_1$ = t-butyl; $R_2$, $R_3$ = methyl is a halogen or $-OSO_2CF_3$) such as dimethylphenylsilyl-, triisopropylsilyl-, trimethylsilyl-, t-butyldiphenylsilyl-, triethylsilyl- or triphenylsilyl-halides or triflates. Solvents and bases used with these silylating agents include, but are not limited to, aprotic solvents such as tetrahydrofuran (THF), dimethylsulfoxide (DMSO), acetonitrile, DMF or methylene chloride ($CH_2Cl_2$) and the like, and bases such as imidazole, dimethylaminopyridine (DMAP), triethylamine (TEA), pyridine or carbonates and the like.

It has also been discovered that the silyl ether of GA7 formed from the above reaction has completely different physical properties from GA4, such as solubility in organic solvents and in water. For example, the silyl ether of GA7 is much more soluble than GA4 in hexane, ether, and dichlo- It has further been discovered that the silyl ethers of each of GA4 and GA7 show different reactivity toward desilylation. Once again, this may be attributed to a thermodynamic selectivity (steric environment of ring A) favoring GA7 reaction. For example, a mixture of the t-butyldimethylsilyl ethers of GA4 and GA7 may be treated with tetrabutylammonium fluoride (2 eq.) in tetrahydrofuran (THF) at room temperature. The silyl ether of GA7 is thereby desilylated, while the silyl ether of GA4 is left intact. Increasing the amount of desilylating agent in excess of two equivalents and/or raising the temperature to above room temperature results in the loss of selectivity, after which both the GA4 and GA7 silyl ethers are completely desilylated (see Scheme II below).

SCHEME 2

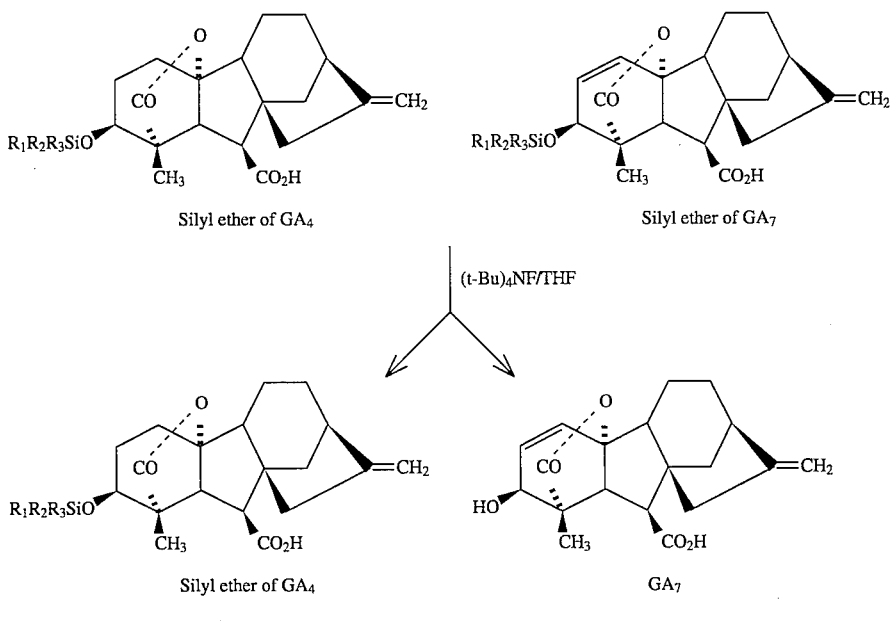

$R_1$ = t-butyl; $R_2$, $R_3$ = methyl

It is expected that the foregoing separatory techniques will also be applicable to the isolation of other gibberellins as well. GA 1 and GA3, for example, which are the 13-hydroxy analogs of GA4 and GA7, respectively, are readily separated using the processes of the invention, as would be any mixture of gibberellins capable of selective silylation or desilylation.

The following examples will serve to further illustrate the present invention.

EXAMPLE 1 a. Selective silylation of GA7 from mixture of GA4/GA7

To a solution of a mixture of GA4 and GA7 (99.3 g. 0.3 mmol) in dimethylformamide (DMF) (480 ml) was added imidazole (61.3 g, 0.9 mol). After imidazole was completely dissolved, t-butyldimethylsilyl chloride (72.4 g, 0.48 mol) was added. The reaction mixture was stirred for 2 days at room temperature under nitrogen. To the mixture was added 400 ml of acetic acid and 500 ml of water. A white solid (silyl ether of GA7) precipitated and was filtered to give 26 g of the silyl ether of GA7. $^1$H NMR (DMSO-d6) 0.10 (s, —SiCH3), 0.88 (S, —Si—t—Bu), 1.08 (S. 18-H3), 2.78 (d, 10Hz, H-5), 3.11 (d, 10Hz, H-6), 4.09 (d. 4Hz, H-3), 4.85 and 4.97 (each br. 17-H2), 5.77 (d,d, 10, 4 Hz, H-2), 6.40 (d, 10Hz, H-1). MS (FAB), 445 (M+H).

To the filtrate was added an excess of water. A white solid was precipitated and filtered to give 38.28 g of crude GA4 which was further purified by suspending the crude GA4 with a solution of Et20/Hexane (1:1) (4 ml/g) to remove the remaining GA7 silyl ether. 31.50 g of GA4 was obtained. The GA4 obtained had physical characteristics consistent with a reference sample. 1H NMR (DMSO-d6), 0.99 (S, 18-H3), 2.39 (d, 12Hz, H-5), 3.02 (d, 11Hz, H-6), 3.55 (m, H-3), 4.84 and 4.96 (each broad, 17-H2), 5.34 (d, 4.5Hz, OH), 12.46 (S,—CO2H). MS(FAB), 333(M+H).

b. Desilylation of Silyl Ether of GA 7

To a solution of the t-butyldimethylsilyl ether of GA7 (26g, 58.6 mmole) in tetrahydrofuran (THF, 50ml) was added a solution of tetrabutylammonium fluoride in THF (117ml, 1.0M solution). The solution was stirred for 8 hours at room temperature under nitrogen. To the reaction mixture was added 1.0 M citric acid solution (50 ml). THF was removed in vacuo, and to the residue was added an excess of 1.0M citric acid. A white solid was precipitated to give 18.36 g of GA7 which was crystallized from acetone/H$_2$O to give 15.20 g of GA7. This GA7 had physical characteristics consistent with a reference sample. $^1$H NMR (DMSO-d6), 1.07 (s, 18-H3), 2.50 (d, 12Hz, H-5), 3.07 (d, 11Hz, H-6), 3.88 (m, H-3), 4.86 and 4.97 (each broad, 17-Hz), 5.57 (broad d, —OH), 5.81 (dd, 10,4Hz, H-2), 6.34 (d, 10Hz, H-1), 12.56 (broad S, —CO2H). MS(FAB), 331(M+1).

EXAMPLE 2 a. Silylation of GA4/GA7 from a Mixture of GA4/GA7

To a solution of a mixture of GA4 and GA7 (44 g. 0.13 mmol) in DMF (155 ml) was added imidazole (90 g, 1.33 mol). After the imidazole was completely dissolved, t-butyldimethylsilyl chloride (100 g, 0.66 tool) was added. The reaction mixture was stirred for 2 days at 45° C. under nitrogen. To the mixture was added 700 ml of acetic acid, 500 ml of THF and 500 ml of water. A white solid (silyl ethers of GA4/GA7) was precipitated and filtered to give 49 g of a mixture of the t-butyldimethylsilyl ethers of GA4/GA7.

b. Selective Desilylation of GA7-Silyl Ether from Mixture of GA4-Silyl Ether and GA7-Silyl Ether To a solution of a mixture of GA4-t-butyldimethylsilyl ether and GA7-t-butyldimethylsilyl ether from Step 2a above (4.45 g, 10 mmol) in THF (20 ml) was added tetrabutylammonium fluoride trihydrate (6.31 g, 20 mmol). The mixture was stirred at room temperature for 8 hours. Acetic acid (20 ml) and water (25 ml) were added to the mixture and a white solid was precipitated to give 1.3 g of GA4-silyl ether. 1H NMR (DMSO-d6), 0.07 (s, —SiCH3), 0.08 (s, —SiCH3), 0.90 (—Si—t—Bu), 0.95 (s, 18-H3), 2.40 (d, 10Hz, H-5), 3.10 (d, 10Hz, H-6), 4.844, and 4.950 (each br. 17-H2). MS(FAB), 447(M+H). To the filtrate was added an excess of water and a white solid was precipitated to give 1.1 g of GA7 which had $^1$H NMR data and physical characteristics consistent with a referenced sample.

The foregoing is merely illustrative of the invention and is not intended to limit the invention to the disclosed processes and compounds. Variations and changes which are obvious to one skilled in the art, such as the use of the process of the invention for the separation of gibberellins closely related in structure to GA4 and GA7, are intended to be within the scope and nature of the invention which are defined in the appended claims.

What is claimed is:

1. A process for separating a gibberellin from a mixture of gibberellins, said mixture selected from the group consisting of (a) a mixture of GA1 and GA3 and (b) a, mixture of GA4 and GA7. said process comprising reacting said mixture with a silylating agent to selectively silylate at least one of said gibberellins.

2. A process according to claim 1 wherein the silylating agent is t-butyldimethylsilyl chloride.

3. A process for separating one of GA4 and GA7 from a mixture thereof, comprising reacting said mixture with a silylating agent.

4. A process according to claim 3 wherein the silylating agent is t-butyldimethylsilyl chloride.

5. A process according to claim 3 comprising the additional steps of selectively hydrolyzing the GA7 silyl ether in the presence of the GA4 silyl ether and separating the GA7 from the GA4 silyl ether.

6. A process according to claim 5 wherein the silylating agent is t-butyldimethylsilyl chloride.

7. A gibberellin selected from the group consisting of GA4 and GA7 which is prepared by the process of claim 3.

8. A gibberellin selected from the group consisting of GA4 and GA7 which is prepared by the process of claim 5.

9. A substantially pure compound of the formula:

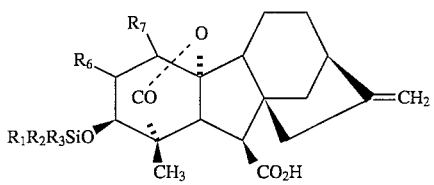

wherein $R_1$, $R_2$ and $R_3$ are independently selected from loweralkyl and aryl, and $R_6$ and $R_7$ are hydrogen or, taken together, form a bond.

10. A compound according to claim 9 wherein $R_1$ is t-butyl and $R_2$ and $R_3$ are methyl.

* * * * *